US012802785B2

(12) United States Patent
Lombardi et al.

(10) Patent No.: US 12,802,785 B2
(45) Date of Patent: Nov. 17, 2026

(54) PREDICTIVE METHOD BASED UPON MACHINE LEARNING FOR THE DEVELOPMENT OF COMPOSITES FOR TIRE TREAD COMPOUNDS

(71) Applicant: Bridgestone Europe NV/SA [BE/BE], Zaventem (BE)

(72) Inventors: Roberto Lombardi, Rome (IT); Paolo Paciotta, Rome (IT); Andrea Guidi, Rome (IT)

(73) Assignee: Bridgestone Europe NV/SA, Zaventem (BE)

( * ) Notice: Subject to any disclaimer, the term of this patent is extended or adjusted under 35 U.S.C. 154(b) by 582 days.

(21) Appl. No.: 18/039,307

(22) PCT Filed: Nov. 30, 2021

(86) PCT No.: PCT/EP2021/083492
§ 371 (c)(1),
(2) Date: May 30, 2023

(87) PCT Pub. No.: WO2022/112584
PCT Pub. Date: Jun. 2, 2022

(65) Prior Publication Data
US 2024/0006033 A1 Jan. 4, 2024

(30) Foreign Application Priority Data
Nov. 30, 2020 (IT) ........................ 102020000029054

(51) Int. Cl.
*G16C 60/00* (2019.01)
*G06N 5/022* (2023.01)
(Continued)

(52) U.S. Cl.
CPC ............ *G16C 60/00* (2019.02); *G06N 5/022* (2013.01); *G06N 20/00* (2019.01); *G16C 20/30* (2019.02); *G16C 20/70* (2019.02)

(58) Field of Classification Search
CPC ..................................................... G16C 60/00
(Continued)

(56) References Cited

U.S. PATENT DOCUMENTS

2020/0019857 A1* 1/2020 Wang ..................... G06F 17/18

FOREIGN PATENT DOCUMENTS

CN 111311321 A 6/2020
JP 2008114783 A 5/2008
(Continued)

OTHER PUBLICATIONS

Self-Paced Probabilistic Principal Component Analysis for Data with Outliers by Zhao et al, arxiv, Apr. 13, 2019 (Year: 2019).*
(Continued)

*Primary Examiner* — Austin Hicks
(74) *Attorney, Agent, or Firm* — Patterson Intellectual Property Law, PC

(57) ABSTRACT

The present invention refers to a computer implemented predictive method based upon machine learning for the development of composites for tyre tread compounds. The method comprises the following steps: —providing a raw data database, namely, a dataset consisting of recipes for already existing composites and of corresponding known dynamic properties, to be used as a reference; —normalizing the data contained in the raw data database according to an iterative procedure; —pre-processing the normalized data by means of Data Mining in order to eliminate aberrant data and to add new fictitious ingredients relating to specific categories of actual ingredients; —training an algorithm based upon automatic learning by means of the pre-pro-
(Continued)

cessed data; —applying said trained algorithm to a set of experimental data that are representative of the recipe of the composite to be tested, for the prediction of the dynamic properties of said composite to be tested.

4 Claims, 6 Drawing Sheets

(51) Int. Cl.
*G06N 20/00* (2019.01)
*G16C 20/30* (2019.01)
*G16C 20/70* (2019.01)

(58) Field of Classification Search
USPC .......................................................... 706/12
See application file for complete search history.

(56) References Cited

FOREIGN PATENT DOCUMENTS

| | | | | |
|---|---|---|---|---|
| JP | 2018147460 | A | | 9/2018 |
| JP | 2020038493 | A | * | 3/2020 |
| KR | 1020200061614 | A | | 6/2020 |

OTHER PUBLICATIONS

International Search Report for corresponding application No. PCT/EP2021/083492, 6 pages, Feb. 11, 2022.

Anonymous: "Normalization (statistics)—Wikipedia", Apr. 18, 2019 (Apr. 18, 2019), XP055721757, Retrieved from the Internet: URL:https://en.wikipedia.org/w/index.php?title=Normalization_(statistics)&oldid=892989526 [retrieved on Aug. 11, 2020] the whole document.

Anonymous: "machine learning—Does it make sense to combine PCA with an artificial neural network?—Data Science Stack Exchange", Jan. 17, 2018 (Jan. 17, 2018), XP055825111, Retrieved from the Internet: URL:https://datascience.stackexchange.com/questions/26683/does-it-make-sense-to-combine-pca-with-an-artificial-neural-network [retrieved on Jul. 16, 2021] the whole document.

Wikipedia Contributors: "Data pre-processing—Wikipedia", Oct. 4, 2020 (Oct. 4, 2020), XP055890401, Retrieved from the Internet: URL:https://en.wikipedia.org/w/index.php?title=Data_pre-processing&oldid=981749180 [retrieved on Feb. 10, 2022] first paragraph; p. 1.

Anonymous: "Data cleansing—Wikipedia", Dec. 4, 2015 (Dec. 12, 2015), XP055350854, Retrieved from the Internet: URL:https://en.wikipedia.org/w/index.php?title=Data_cleansing&oldid=693707897 [retrieved on Mar. 2, 2017] the whole document.

* cited by examiner

STEP 1 – DATA NORMALIZATION PROCEDURE + DATA MINING PRE-PROCESSING

LAB HISTORICAL DATABASE

| Recipe Number | Compound Recipes: Content [PHR] Ingredient #1 | Ingredient #2 | Ingredient #3 | - | - | Ingredient #m | Lab mesurements: tanδ measurement 0°C | 30°C | 60°C | E' measurement 0°C | 30°C | 60°C |
|---|---|---|---|---|---|---|---|---|---|---|---|---|
| **#1 †** | **50** | **6** | **1.5** | | | **4** | $T_{1,0}$ | $T_{1,30}$ | $T_{1,60}$ | $E_{1,0}$ | $E_{1,30}$ | $E_{1,60}$ |
| #2 | 60 | 1 | 1.5 | | | 3 | $T_{2,0}$ | $T_{2,30}$ | $T_{2,60}$ | $E_{2,0}$ | $E_{2,30}$ | $E_{2,60}$ |
| **#3 †** | **50** | **6** | **1.5** | | | **4** | $T_{3,0}$ | $T_{3,30}$ | $T_{3,60}$ | $E_{3,0}$ | $E_{3,30}$ | $E_{3,60}$ |
| #4 | 80 | 8 | 1.5 | | | 2 | $T_{4,0}$ | $T_{4,30}$ | $T_{4,60}$ | $E_{4,0}$ | $E_{4,30}$ | $E_{4,60}$ |
| - | | | | | | | | | | | | |
| - | | | | | | | | | | | | |
| - | | | | | | | | | | | | |
| **#(n-1) †** | **50** | **6** | **1.5** | | | **4** | $T_{n-1,0}$ | $T_{n-1,30}$ | $T_{n-1,60}$ | $E_{n-1,0}$ | $E_{n-1,30}$ | $E_{n-1,60}$ |
| #n | 40 | 15 | 1 | | | 3 | $T_{n,0}$ | $T_{n,30}$ | $T_{n,60}$ | $E_{n,0}$ | $E_{n,30}$ | $E_{n,60}$ |

These recipes have been physically prepared and tested.

† These recipes have been selected as reference (repeated) recipes.

Lab Testing

Data Normalization Procedure + DATA MINING

*FIG. 1A*

STEP 2 – ARTIFICIAL NEURAL NETWORK TRAINING

LAB HISTORICAL DATABASE

| | Compound Recipes | | | | | | Lab mesurements | | | | | |
|---|---|---|---|---|---|---|---|---|---|---|---|---|
| Recipe Number | Content [PHR] | | | | | | tanδ measurement | | | E' measurement | | |
| | Ingredient #1 | Ingredient #2 | Ingredient #3 | - | - | Ingredient #m | 0°C | 30°C | 60°C | 0°C | 30°C | 60°C |
| **#1 †** | **50** | **6** | **1.5** | | | **4** | $T_{1,0}$ | $T_{1,30}$ | $T_{1,60}$ | $E_{1,0}$ | $E_{1,30}$ | $E_{1,60}$ |
| #2 | 60 | 1 | 1.5 | | | 3 | $T_{2,0}$ | $T_{2,30}$ | $T_{2,60}$ | $E_{2,0}$ | $E_{2,30}$ | $E_{2,60}$ |
| **#3 †** | **50** | **6** | **1.5** | | | **4** | $T_{3,0}$ | $T_{3,30}$ | $T_{3,60}$ | $E_{3,0}$ | $E_{3,30}$ | $E_{3,60}$ |
| #4 | 80 | 8 | 1.5 | | | 2 | $T_{4,0}$ | $T_{4,30}$ | $T_{4,60}$ | $E_{4,0}$ | $E_{4,30}$ | $E_{4,60}$ |
| - | | | | | | | | | | | | |
| - | | | | | | | | | | | | |
| - | | | | | | | | | | | | |
| **#(n-1) †** | **50** | **6** | **1.5** | | | **4** | $T_{n-1,0}$ | $T_{n-1,30}$ | $T_{n-1,60}$ | $E_{n-1,0}$ | $E_{n-1,30}$ | $E_{n-1,60}$ |
| #n | 40 | 15 | 1 | | | 3 | $T_{n,0}$ | $T_{n,30}$ | $T_{n,60}$ | $E_{n,0}$ | $E_{n,30}$ | $E_{n,60}$ |

Lab Testing

These recipes have been physically prepared and tested.

† These recipes have been selected as reference (repeated) recipes.

Data Normalization Procedure + DATA MINING

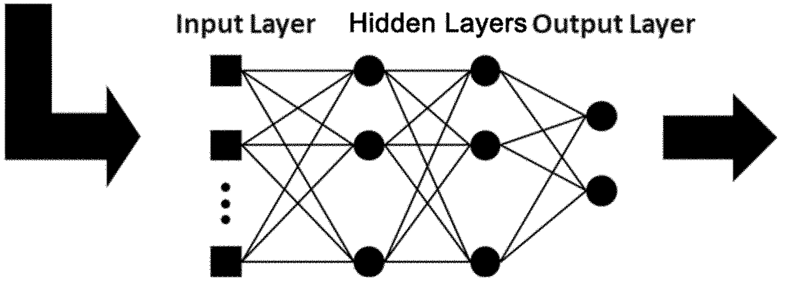

Training Complete ! Algorithm ready for predictions

*FIG. 1B*

STEP 3 – PREDICTION

| Compound Recipes | | | | | | | Lab mesurements | | | | | |
|---|---|---|---|---|---|---|---|---|---|---|---|---|
| Recipe Number | Content [PHR] | | | | | | tanδ measurement | | | E' measurement | | |
| | Ingredient #1 | Ingredient #2 | Ingredient #3 | - | - | Ingredient #m | 0°C | 30°C | 60°C | 0°C | 30°C | 60°C |
| #1 | 50 | 10 | 3 | | | 4 | ? | ? | ? | ? | ? | ? |
| | | | | | | | | | | | | |

Experimental sessions are linked if they share >=1 input

PREDICTIVE METHOD BASED UPON MACHINE LEARNING FOR THE DEVELOPMENT OF COMPOSITES FOR TIRE TREAD COMPOUNDS

The present invention refers to a predictive method for the dynamic properties of rubber compounds that is based upon machine learning, to be implemented therefore by means of an electronic computer, for the development of composites for tire tread compounds.

BACKGROUND

The present invention is in the tire manufacturing sector, in particular with reference to the determination of the composition of those rubber compounds used for manufacturing tire treads.

The dynamic properties of these rubber compounds (for example tan δ and E') play a key role in determining tire performance, especially those that relate to energy dissipation (for example wet braking, dry braking and the Coefficient of Rolling Resistance (RRC).

These properties are ensured by the characteristics of the recipes used for the composites, in particular in terms of the ingredients, the quantity thereof and the particular synergies that are established between two or more thereof.

Commonly, the correct formulation of the recipes used for composites must go through several validation steps in the laboratory in order to first find the right technological package and then optimize the formulation by means of progressive fine-tuning until the objective is fully achieved.

Each of these iterative experimental campaigns leads, from the product point of view, to an increase in lead-times and costs in developing the product (time to market) and, from the data point of view, to the generation of a database with intrinsic variability due to random noise within the measurements made during the various test campaigns.

The expectations for the performance of the product, in relation to energy dissipation (for example wet braking, dry braking and RRC), is determined by evaluating the dynamic properties of the rubber compound (for example tan δ and E'). Such an evaluation requires extensive laboratory testing in order to reach validation of the composite and requires time and resources.

The object of the present invention is, therefore, to solve those problems left unresolved by the prior art, by providing a process as defined in claim 1.

In particular, an object of the present invention is that of simulating laboratory tests, in order to provide an accurate estimate of some of the significant dynamic properties of composites for the production of rubber compounds for tires without the need to perform any physical tests. These properties are, for example, tan δ and E', which represent key parameters to determine the performance of those products that are associated with energy dissipation (for example wet braking, dry braking and RRC).

Further characteristics of the present invention are defined in the corresponding dependent claims.

On the other hand, the use of a software tool that can predict the behavior of composites, and therefore tire performance, allows for:

- a significant reduction in recurring costs (raw materials, labor, etc. . . . );
- optimized execution capacity and quality of laboratory tests (making it possible to allocate manpower to other activities);
- shorter time to market for new products;
- increased predictive precision in relation to known methodologies.

Other clear advantages over the prior art, together with the characteristics and usages of the present invention, will become clear from the following detailed description of the preferred embodiments thereof, given purely by way of a non-limiting example.

BRIEF DESCRIPTION OF THE FIGURES

Reference will be made to the drawings in the attached figures, wherein:

FIGS. 1A, 1B, 1C show, by way of example, the process of the present invention;

DETAILED DESCRIPTION OF POSSIBLE EMBODIMENTS OF THE INVENTION

The present invention will be described below with reference to the above figures.

A methodology will therefore be described for the prediction of dynamic properties (for example Tan δ and E') of composites that can be used for the production of rubber compounds for tires.

In general terms, the process involves the following procedure:

- generation of a raw data database, namely, a dataset consisting of recipes for already existing composites and of corresponding known dynamic properties (N experimental sessions, each containing tests on $M_N$ compounds);
- a procedure for the iterative normalization of the data contained in the raw data database;
- the pre-processing of the normalized data by means of Data Mining;
- the training and application of an algorithm based upon automatic learning (machine learning, for example an artificial neural network).

In particular, after a step of training the model using the dataset contained in the normalized and pre-processed database as described above, it is possible to predict the dynamic properties of the composite with greater precision than by directly applying an algorithm straight to the raw data in the database.

In fact, in this way, it is possible to drastically reduce the effect, on the predictive precision, of database noise and the intrinsic variability of the data.

In fact, by means of the procedure for the iterative normalization of the data, operating by means of data relating to multiple laboratory tests on the same species of reference (at least one of the $M_N$ compounds present in each of the N experimental sessions), the aim is to reduce the intrinsic experimental variability. Indeed, each repeated test, performed during specific experimental sessions, is used to estimate the rate of variability due to these specific experimental conditions.

Furthermore, the pre-processing procedure (Data Mining) is used to improve the accuracy of predictions by developing new capabilities, removing aberrant data and performing a principal component analysis (PCA).

Finally, the machine learning algorithm, for example an artificial neural network (ANN), predicts some of the main dynamic properties of the composites under examination, for example, as already indicated, the tan δ versus temperature trend and the E' versus Temperature trend.

Figure 1C:
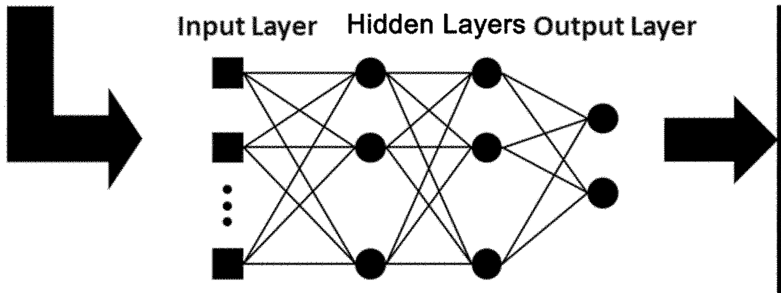
Figure 1C:
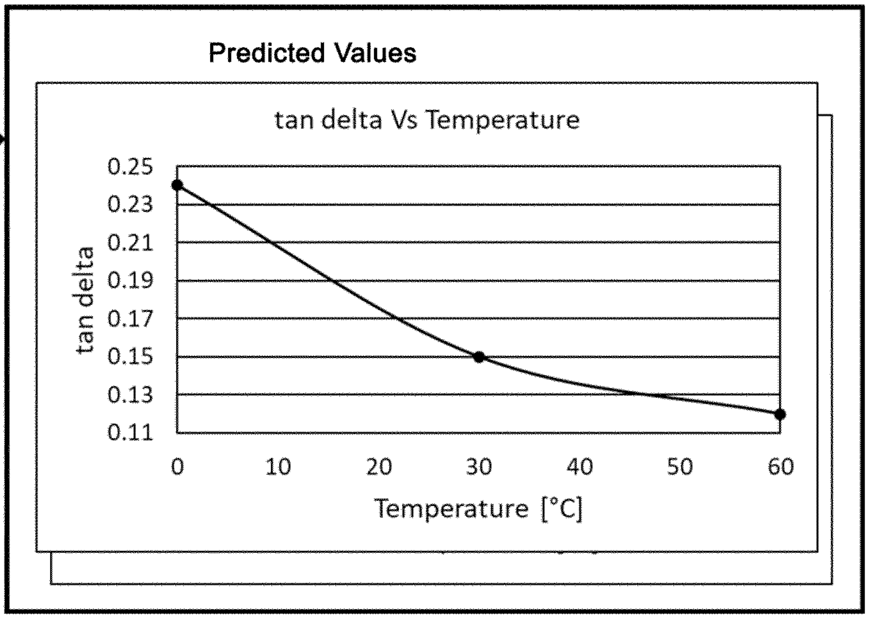

FIGS. 1A, 1B, 1C show, by way of example, the process of the present invention.

Theoretical Background

During the dynamic mechanical analysis (DMA), a sinusoidal force (stress σ) is applied to a material and the resulting displacement (deformation) is measured. If the material is perfectly elastic, the resulting tension and stress are perfectly in phase. If the material is purely a viscous fluid, a 90 degrees' deformation phase lag, with respect to stress, is observed.

Viscoelastic polymers have intermediate characteristics whereby some phase delays occur during DMA tests. In this context:

E' it is the storage module, measuring the stored energy, i.e., the elastic portion;

tan δ is the loss module, measuring the energy dissipated as heat, i.e., the viscous portion.

Figure 2:
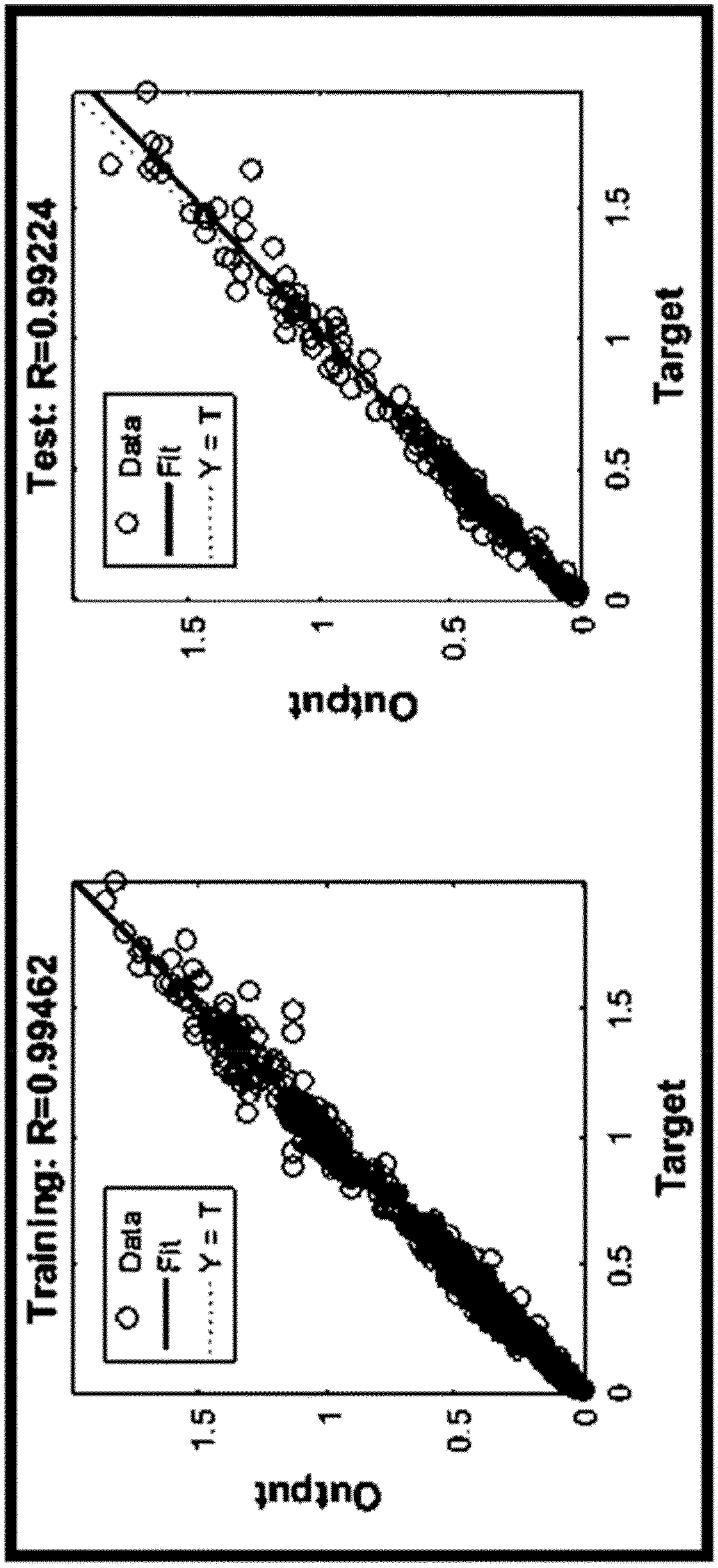
FIG. 2 shows a scatter plot of the original tan δ values versus the expected tan δ values.

The results are validated by comparing the values of tan δ and E', as predicted by the developed algorithm, with those known experimentally for a plurality of new experimental recipes, which were obviously not used to feed the neural network (ANN) during the training step. FIG. 2 shows the scatter plot of the original tan δ values versus the predicted tan δ values as an example of training and the performance of the test set. As can be seen, both scatter plots are characterized by a high value of $R^2$ (>0.99).

It should be noted that, according to the invention, important preprocessing steps are performed before the ANN algorithm training step. More specifically, the aforementioned data normalization procedure+the preprocessing step by means of data mining.

Iterative Data Normalization Procedure

This normalization procedure has demonstrated the most efficient improvement. In this type of application, due to the repeated experimental sessions, it is usually possible to observe high variability as regards the target properties. Indeed, some recipes are often repeated in several experimental sessions and the target properties thereof sometimes demonstrate significant differences. By investigating all of the N experimental sessions performed, it is possible to find different recipes, amongst the $M_N$ possible recipes, that can be used to reduce this variability in relation to the experimental sessions.

The normalization is carried out on each experimental session by referring to those physical properties of the recipe that are common to the various experimental sessions. If such a recipe cannot be used to normalize some of the experimental sessions, insofar as it is not included in them, a new recipe will be selected, in such a way that it is included in at least one already normalized experimental session and in those experimental sessions still to be normalized. By means of this selection it will be possible to iteratively extend and apply the normalization to new experimental sessions.

Figure 3:
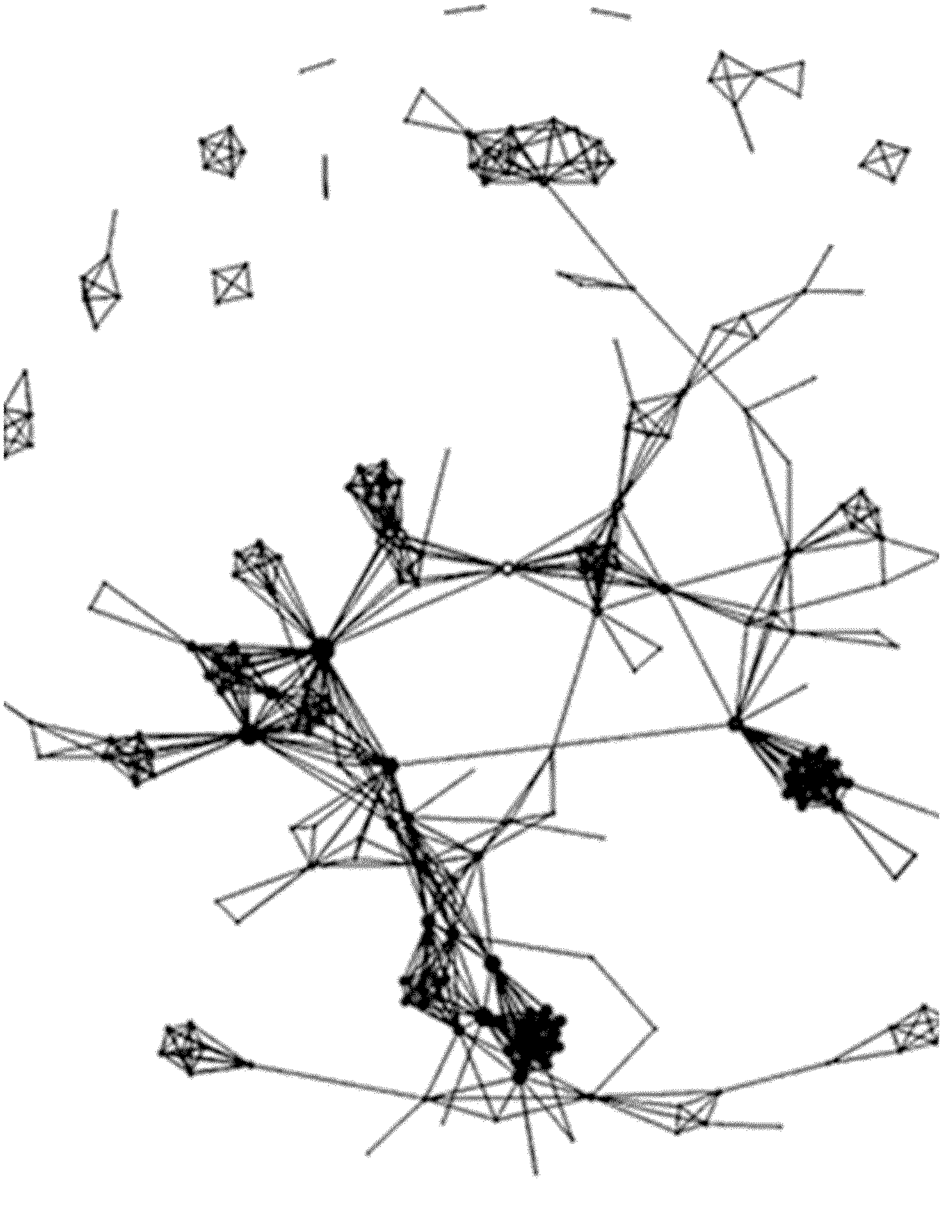
FIG. 3 represents the "connections", i.e., the possibilities of reducing the variability, between the various experimental sessions.

FIG. 3 shows a representation of the "connections", namely the possibilities of reducing the variability by means of common formulations (recipes), between the various experimental sessions. The spots represent the experimental sessions, while the lines represent the "connections", i.e., the methods of normalization of the experimental sessions by means of the reference compounds/formulations (recipes). The graph represents all possible ways to "connect" (i.e., normalize) the experimental sessions, and thus to reduce the variability thereof. As can be understood by looking at the proposed graph, each experimental session can be linked to many other sessions. Such a procedure can therefore be performed iteratively in order to reduce the variability in as many experimental sessions as possible.

From a mathematical point of view, these connections can be made in many ways and therefore different normalization procedures can be used.

According to the invention, each target property (i.e., for example, tan δ and E') is divided by those corresponding to the recipes used as a reference in the experimental sessions.

From an operational point of view, the iterative normalization procedure is performed as follows:

1. The selection of all experimental sessions that contain the recipe $F_{MR}$ (Most Repeated Formulation) that is most repeated in the dataset.
2. The physical properties of all the formulations included in all of the experimental sessions, selected in the previous point, are normalized by referring to the corresponding properties of the recipe $F_{MR}$;
3. Each normalized experimental session $SS_{Normalized}$, is connected, according to the graph of FIG. 3, by means of a recipe $F_C$ (Common Formulation), to a non-normalized experimental session $SS_{NotNormalized}$, therefore:
   a. The physical properties of the recipe $F_C$ included in $SS_{NotNormalized}$ are normalized by taking as reference the physical properties of $F_C$ included in $SS_{Normalized}$;
   b. The physical properties of all of the recipes included in $SS_{NotNormalized}$ are normalized by taking as reference those physical properties of $F_C$ included in $SS_{NotNormalized}$ (which has already been pre-normalized);
4. The procedure described in point 3 is applied iteratively to all the experimental sessions according to the graph of FIG. 3.

It is important to highlight that, according to the invention and contrary to what happens in the known art, data normalization is not applied to the data set as a whole. The normalization procedure is applied in a specific and targeted way to each experimental session, and is developed in order to make each individual experimental session comparable to the others, thereby forming the data set as a whole. This objective is achieved by reducing the variability in relation to the experimental session. This means that what is generally discouraged in the known art, insofar as it introduces harmful non-linearities, namely the normalization of different data sets in different ways, according to the invention is used and exploited in order to achieve the desired results by means of the implementation of iterative normalizations that are determined according to the connections of the graph in FIG. 3.

The normalization procedure can be described as:

$$\bar{y}_{a,b,c} = \frac{y_{a,b,c}}{y_{a,ref_a,c}}$$

wherein: a stands for the a-th experimental session, b stands for the b-th example belonging to the specific experimental session, c stands for the c-th target property, refi indicates the reference example of the a-th experimental session and $\bar{y}_{a,b,c}$ stands for y normalized.

The following Table 1 shows the difference between performing the data normalization procedure or not in terms of accuracy.

In doing so, accuracy is defined as the percentage of recipes that show a percentage prediction error that is lower than the target percentage error. The E' value prediction model showed an increase in accuracy greater than 30% by virtue of the application of the data normalization procedure (see the DELTA column), while the tan δ value prediction model showed an increase in precision greater than 11%.

TABLE 1

| | | Accuracy (% of population within the target error) | | |
|---|---|---|---|---|
| Target property | % Target error | Without normalization | With normalization | DELTA |
| E' @ 0° | Err <12% | 28.57% | 68.57% | 40.00% |
| E' @ 30° | Err <12% | 34.28% | 65.71% | 31.43% |
| E' @ 60° | Err <12% | 37.14% | 68.58% | 31.44% |
| tanδ @ 0° | Err <7% | 71.43% | 82.86% | 11.43% |
| tanδ @ 30° | Err <7% | 68.57% | 80.00% | 11.43% |
| tanδ @ 60° | Err <7% | 57.14% | 77.14% | 20.00% |

This table shows the predictive precision of E' and tan δ with the aim of highlighting the impact of the data normalization procedure. Normalized data processing improves the predictive performance of each individual target property. Interestingly, the normalization procedure introduces a 40% improvement in the prediction accuracy of E' @ 0° (from 28.57% accuracy without normalization to 68.57% accuracy with normalized data).

Pre-Processing Using Data Mining

The accuracy of the prediction is greatly improved when a correct data mining operation (iterative normalization, aberrant data removal, PCA) is performed on the experimental dataset used to build the algorithm during the "training step". Indeed, PCA is able to remove those ingredients that do not affect the target properties (for example tan δ and E') from the recipes of the training dataset and to add new fictitious ingredients, created specifically in order to emphasize the informative content of the dataset.

With the term informative contribution of a feature (and therefore, by extension, of the dataset) reference is being made to the fact that the effect thereof upon the physical properties being predicted is well interpreted by the model, again in relation to the quantity and interaction thereof with other ingredients, in line with the performance thereof. A correct increase of 2 Mpa in relation to one property of those in question following an increase-decrease of a certain ingredient is a ratio that, if properly interpreted by the model, is a positive informative contribution.

The anomalous data removal procedure is designed to be implemented by taking into account both each individual experimental session alone and all of the various experimental sessions jointly. This dual nature of the procedure makes it possible to take advantage of every single session.

In order to add new fictitious ingredients, with the aim of facilitating the subsequent creation of predictive models, the original ingredients have been divided into certain categories, i.e., polymers, fillers, accelerators, etc. PCA was then applied to each ingredient category in order to estimate a new fictitious ingredient that could enhance the informative content of that particular ingredient category. In this context, therefore, it is possible to define as a fictitious ingredient a linear combination of the actual ingredients, as supplied to the PCA, that is such that it can emphasize the informative contribution of that specific category of ingredients. This linear combination therefore combines the informative contribution of the initial ingredients. From this it follows that the informative contribution made by the fictitious ingredient summarizes and amplifies the informative contribution of the initial ingredients. Finally, for each category of ingredients, the fictitious ingredients determined in such a way have been added to the input list (i.e., ingredients) that the prediction algorithm has the task of processing and, therefore, both the original informative contributions and those amplified in the fictitious ingredient are subject to analysis.

Management of Physical Conditions in Relation to the Dynamic Properties E' and tan δ

Figure 4:
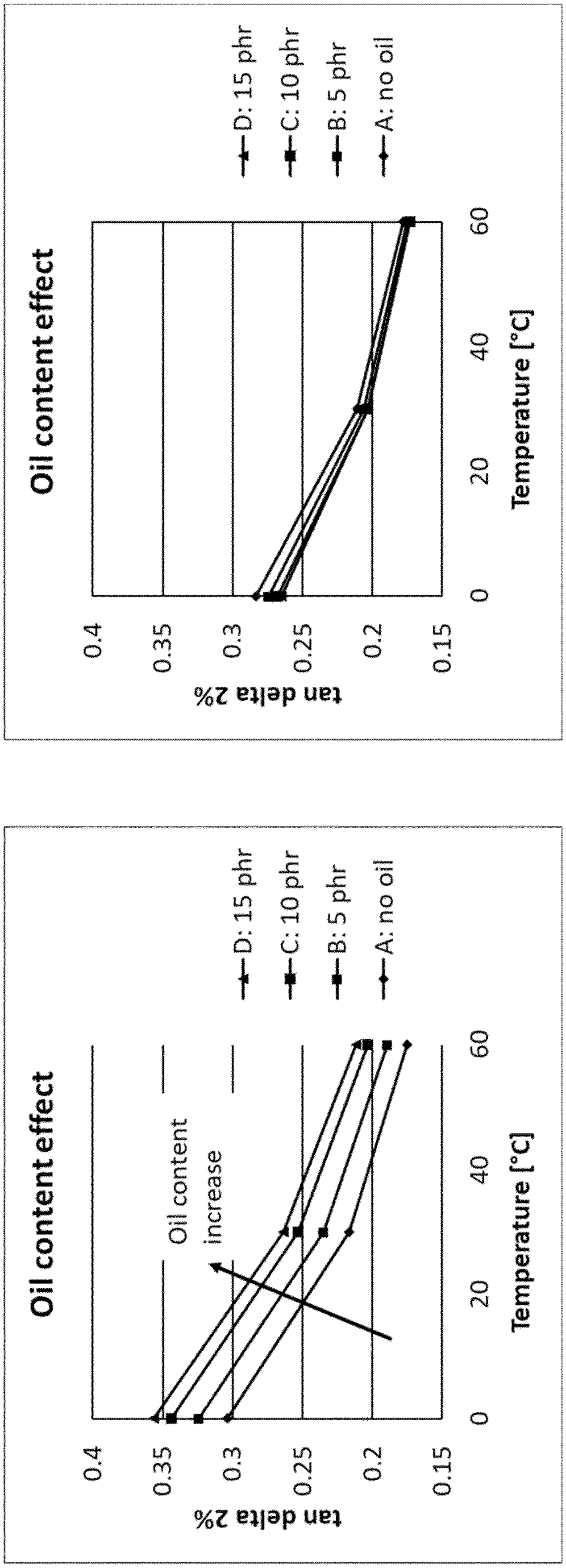
FIG. 4 shows two graphs representing the quality of the prediction with and without the application of physical constraints.

Refer now to FIG. 4 and to the following Table 2. The quality of the predictions also depends upon a series of physical conditions that should be satisfied by the algorithm during the "training step".

In particular, the predictions become more reliable when the model is forced to simultaneously satisfy the following significant physical constraints:

i. $\frac{\partial y}{\partial T} < 0 \;\&\; y_{(60^\circ)} > 0$ (monotonous and positive trend of $y_{60^\circ}$ versus temperature ii. $\frac{\partial^2 y}{\partial x^2} > 0$ (convexity of the trend of $y$ versus temperature)

iii. $y_{30^\circ} = y_{0^\circ}(1 - R_{0^\circ/30^\circ})$ iv. $y_{60^\circ} = y_{0^\circ}(1 - R_{0^\circ/60^\circ})$ wherein $$R_{i^\circ/j^\circ} = \frac{y_{i^\circ} - y_{j^\circ}}{y_{i^\circ}}$$

and y stand for E' and tan δ respectively.

The factor $R_{i^\circ/j^\circ}$ is introduced in order to normalize the target functions tan δ (t) and E'(t). The normalization $R_{i^\circ/j^\circ}$ is a necessary condition in order to ensure that the algorithm applies an equal "weight" to all temperatures, although the absolute values of tan δ(T) and E'(T) decrease. These constraints are applied by means of a weight/penalty logic to the cost function to be minimized during the training of the model itself. This means that the cost function is conveniently multiplied by:

- a coefficient equal to 1 if all of the physical constraints are respected;
- a coefficient greater than 1 if one or some of the physical constraints are not respected.

The purpose of this procedure is to promote models that are capable of making predictions that respect the physical constraints.

Although both methodologies (with and without constraints) correctly predict the decay tendency of tan δ versus temperature, only the constrained model correctly estimates the increase in tan δ with an oil content.

TABLE 2

| | CPD | A | B | C | D |
|---|---|---|---|---|---|
| Recipes [phr] | NR | 80 | 80 | 80 | 80 |
| | BR | 20 | 20 | 20 | 20 |
| | CB | 50 | 50 | 50 | 50 |
| | 6PPD | 1.5 | 1.5 | 1.5 | 1.5 |
| | SULFUR | 1 | 1 | 1 | 1 |
| | ACCELERANT | 2 | 2 | 2 | 2 |
| | RAE OIL | 0 | 5 | 10 | 15 |
| Constrained model | tanδ 0° | 0.304 | 0.324 | 0.344 | 0.356 |
| | tanδ 30° | 0.217 | 0.235 | 0.253 | 0.264 |
| | tanδ 60° | 0.175 | 0.189 | 0.203 | 0.212 |
| Unconstrained model | tanδ 0° | 0.283 | 0.274 | 0.268 | 0.265 |
| | tanδ 30° | 0.211 | 0.206 | 0.203 | 0.203 |
| | tanδ 60° | 0.178 | 0.175 | 0.173 | 0.174 |

The present invention has heretofore been described with reference to the preferred embodiments thereof. It is intended that each of the technical characteristics implemented in the preferred embodiments described herein, purely by way of example, can advantageously be combined, in ways other than that described heretofore, also with other characteristics in order to give form to other embodiments which also belong to the same inventive nucleus and that all fall within the scope of protection afforded by the claims recited hereinafter.

The invention claimed is:

1. A computer-implemented method for predicting dynamic properties of a composite to be tested for the production of tire tread compounds, the method comprising:

providing a raw data database comprising a dataset of recipes for already existing composites and of corresponding known dynamic properties, and representative of a plurality of experimental sessions, wherein each recipe in the dataset has a respective composite formulation, and one or more of the composite formulations in the dataset are repeated across two or more of the plurality of experimental sessions;

normalizing data contained in the raw data database according to an iterative procedure, according to at least sub-steps comprising:

a) selecting all experimental sessions containing a recipe with a most repeated composite formulation in the dataset;

b) normalizing physical properties of all formulations included in all of the selected experimental sessions, by referring to corresponding properties of the recipe with the most repeated composite formulation;

c) normalizing physical properties of common formulation recipes included in not-normalized experimental sessions, by taking as reference the dynamic properties of common formulation recipes included in normalized experimental sessions;

d) normalizing physical properties of all recipes included in the not-normalized experimental sessions, by taking as reference those dynamic properties of common formulation recipes included in not-normalized experimental sessions which have already been pre-normalized; and e) iteratively applying sub-steps c) and d) to each of the plurality of experimental sessions;

pre-processing the normalized data by data mining to eliminate aberrant data and to estimate new ingredients relating to specific categories of actual ingredients, wherein the estimated ingredients are added by:

dividing the actual ingredients into ingredient categories;

applying principal component analysis to each ingredient category to estimate a respective ingredient as a linear combination of the actual ingredients that combines informative information of such actual ingredients, as supplied to the principal component analysis, wherein the estimated ingredient demonstrates an informative contribution of its respective category of ingredients; and for each ingredient category, adding the respective estimated ingredient to an input list of ingredients to be processed, wherein both of original informative contributions and those further demonstrated by the estimated ingredient are subject to analysis;

training an algorithm based upon automatic learning via the pre-processed data;

applying the trained algorithm to a set of experimental data representative of the recipe of the composite to be tested, for prediction of dynamic properties of the composite to be tested.

2. The method of claim 1, wherein the dynamic properties are a loss tangent tan δ and a storage modulus E' of the composite to be tested.

3. The method of claim 1, wherein a weight/penalty logic, applied to calculation of a cost function to be minimized during the training step, imposes physical constraints upon the dynamic properties to be predicted, wherein the cost function is multiplied by:

a coefficient equal to 1 if all of the physical constraints are respected; or a coefficient greater than 1 if one or more of the physical constraints are not respected.

4. The method of claim 3, wherein the constraints are represented by:

i. $\frac{\partial y}{\partial T} < 0 \;\&\; y_{(60^\circ)} > 0$ (monotonous and positive trend of $y_{60^\circ}$ versus temperature;

ii. $\frac{\partial^2 y}{\partial x^2} > 0$ (convexity of the trend of $y$ versus temperature);

iii. $y_{30^\circ} = y_{0^\circ}(1 - R_{0^\circ/30^\circ})$;

iv. $y_{60^\circ} = y_{0^\circ}(1 - R_{0^\circ/60^\circ})$;

wherein T is temperature, wherein y represents a loss tangent tanδ or a storage modulus E' of the composite to be tested, wherein $y_{0^\circ}$ is a value of y at 0 degrees, $y_{30^\circ}$ is a value of y at 30 degrees, and $y_{60^\circ}$ is a value of y at 60 degrees, and wherein $$R_{0^\circ/30^\circ} = \frac{y_{0^\circ} - y_{30^\circ}}{y_{0^\circ}} \text{ and } R_{0^\circ/60^\circ} = \frac{y_{0^\circ - 60^\circ}}{y_{0^\circ}}.$$

* * * * *